(12) United States Patent
Kim et al.

(10) Patent No.: US 11,523,921 B2
(45) Date of Patent: Dec. 13, 2022

(54) MULTIFUNCTIONAL BIOIMPLANTABLE STRUCTURE AND METHOD OF PREPARING THE SAME

(71) Applicants: RESEARCH & BUSINESS FOUNDATION SUNGKYUNKWAN UNIVERSITY, Suwon-si (KR); KOREA INSTITUTE OF SCIENCE AND TECHNOLOGY, Seoul (KR)

(72) Inventors: Tae Il Kim, Seoul (KR); So Ri Lee, Suwon-si (KR); Ji Yeon Lee, Seoul (KR); Gyo Yeon Hwang, Seoul (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 559 days.

(21) Appl. No.: 15/945,397

(22) Filed: Apr. 4, 2018

(65) Prior Publication Data

US 2018/0289516 A1    Oct. 11, 2018

(30) Foreign Application Priority Data

Apr. 6, 2017 (KR) .................. 10-2017-0044570

(51) Int. Cl.
*A61L 31/10* (2006.01)
*A61L 31/14* (2006.01)
(Continued)

(52) U.S. Cl.
CPC .............. *A61F 2/90* (2013.01); *A61K 9/0097* (2013.01); *A61K 31/704* (2013.01); *A61L 31/022* (2013.01); *A61L 31/088* (2013.01); *A61L 31/10* (2013.01); *A61L 31/146* (2013.01); *A61L 31/148* (2013.01); *A61L 31/16* (2013.01); *A61F 2240/001* (2013.01); *A61F 2250/0067* (2013.01); *A61F 2250/0068* (2013.01); *A61L 2420/08* (2013.01); *B05D 1/18* (2013.01);
(Continued)

(58) Field of Classification Search
None
See application file for complete search history.

(56) References Cited

U.S. PATENT DOCUMENTS 6,000,411 A * 12/1999 Lee ...................... C11D 7/3209
                                                    257/E21.228
7,320,709 B2 * 1/2008 Felt ....................... A61F 2/3872
                                                    623/20.16
(Continued)

FOREIGN PATENT DOCUMENTS

KR    20100077770 A    7/2010

OTHER PUBLICATIONS

"Transplant" definition accessed online on Jun. 5, 2020 at Merriam-Webster.com. (Year: 2020).*

*Primary Examiner* — Casey S Hagopian
(74) *Attorney, Agent, or Firm* — NSIP Law

(57) ABSTRACT

The present disclosure provides a method for producing a multifunctional implantable structure, the method having: preparing an implantable base; coating a polymer layer on the base, wherein the polymer layer is partially curable; curing the polymer layer such that the polymer layer has cured and non-cured portions; and dry-etching the polymer layer to remove the non-cured portion thereof, to allow the polymer layer to have a nano-turf structure having pores defined therein.

19 Claims, 14 Drawing Sheets

(51) Int. Cl.
*A61L 31/16* (2006.01)
*A61L 31/08* (2006.01)
*A61L 31/02* (2006.01)
*A61K 9/00* (2006.01)
*A61F 2/90* (2013.01)
*A61K 31/704* (2006.01)
*B05D 3/06* (2006.01)
*B05D 1/18* (2006.01)
*B05D 3/10* (2006.01)
*B05D 3/12* (2006.01)

(52) U.S. Cl.
CPC .............. *B05D 3/067* (2013.01); *B05D 3/107* (2013.01); *B05D 3/12* (2013.01)

(56) References Cited

U.S. PATENT DOCUMENTS

| | | | |
|---|---|---|---|
| 2002/0002246 A1* | 1/2002 | Wang | A61L 27/26 525/240 |
| 2003/0064168 A1* | 4/2003 | Kato | C09D 183/04 528/33 |
| 2003/0211129 A1* | 11/2003 | Spillman, Jr. | A61L 29/085 424/423 |
| 2005/0051785 A1* | 3/2005 | Erchak | B82Y 20/00 257/98 |
| 2010/0168506 A1* | 7/2010 | Moon | A61L 31/148 600/36 |
| 2011/0245905 A1* | 10/2011 | Weber et al. | A61L 31/044 623/1.15 |

\* cited by examiner

MULTIFUNCTIONAL BIOIMPLANTABLE STRUCTURE AND METHOD OF PREPARING THE SAME

CROSS-REFERENCE TO RELATED APPLICATION

This application claims the benefit of Korean patent application No. 10-2017-0044570 filed on Apr. 6, 2017, the entire content of which is incorporated herein by reference for all purposes as if fully set forth herein.

FIELD OF INVENTION

The present disclosure relates to an implantable structure and a method for producing the same. More particularly, the present disclosure relates to a multifunctional implantable structure having excellent drug loading ability and capable of selective release of loaded drug therein, and a method for producing the structure.

BACKGROUND OF INVENTION

Biocompatible nano-surface modification techniques applied to implantable devices to enhance biocompatibility of a material by controlling reaction between cells and an interface of the material that directly or indirectly affect the cells or tissues are increasingly being studied Conventional biocompatible nano-surface modification techniques may be classified, based on their processing, into a method of controlling micro-roughness using techniques such as chemical acid etching and anodic oxidation of biocompatible materials (for example, $TiO_2$ and $Al_2O_3$), and a method of modifying a surface shape using electron beam, laser lithography, block copolymer lithography, and the like.

The method of using the acid etching or anodization techniques has a potential advantage of forming pores to achieve a large surface portion. However, in order to make the above-mentioned structure, the method includes multiple steps of 1) depositing a protective metal layer, 2) depositing a metal layer for anodization, 3) anodizing an aluminum oxide or titanium oxide, 4) conducting hydrophilic plasma treatment, and 5) injecting a drug and a functional substance. Thus, the method may be complicated.

Meanwhile, although the method of using the electron beam or laser lithography has an advantage that a surface of a bio-base material is directly modified, the method requires a large amount of energy and time to etch a metal having a high mechanical modulus. Although a self-assembly method using a block copolymer easily control the pore size, the structure may be deformed during a solvent or thermal annealing process to selectively remove portions corresponding to pores to form the pores.

Therefore, in order to solve the problems, there is a need for an implantable structure configured to selectively inhibit cell proliferation, and easily control loading and releasing of the drug.

SUMMARY OF INVENTION

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

A purpose of the present disclosure is to provide an implantable structure capable of loading a drug therein in a reliable manner, controlling release of the loaded drug, and selectively inhibiting cell proliferation.

In a first aspect of the present disclosure, there is provided a method for producing a multifunctional implantable structure, the method comprising: preparing an implantable base; coating a polymer layer on the base, wherein the polymer layer is partially curable; curing the polymer layer such that the polymer layer has cured and non-cured portions; and dry-etching the polymer layer to remove the non-cured portion thereof, to allow the polymer layer to have a nano-turf structure having pores defined therein.

In one embodiment of the method, the method further comprises, after the dry-etching, immersing the polymer layer in a drug such that the pores are loaded with the drug.

In one embodiment of the method, the method further comprises, after the immersing, coating a metal layer as a passivation layer on the polymer layer.

In one embodiment of the method, the polymer layer is photo-curable.

In one embodiment of the method, the polymer layer is biodegradable.

In one embodiment of the method, the polymer layer includes polysiloxane-acrylate (PSA).

In one embodiment of the method, the metal layer is biocompatible

In one embodiment of the method, the metal layer includes at least one selected from a group consisting of gold, silver, titanium, and molybdenum.

In one embodiment of the method, coating the metal layer includes coating an amorphous metal layer on the polymer layer.

In one embodiment of the method, the metal layer has pores defined therein, wherein the drug is released through the pores defined in the metal layer.

In one embodiment of the method, the metal layer is controlled in a temperature thereof by near-infrared rays (NIR) to control a release rate of the drug.

In a second aspect of the present disclosure, there is provided a multifunctional implantable structure comprising: an implantable base; and a nano-turf structure formed on the base, wherein the nano-turf structure includes: a polymer layer having pore defined therein, and a metal layer formed on the polymer layer, wherein the metal layer has pore defined therein, wherein the pores in the polymer layer are loaded with a drug.

In one embodiment of the multifunctional implantable structure, the polymer layer is photo-curable.

In one embodiment of the multifunctional implantable structure, the polymer layer is biodegradable.

In one embodiment of the multifunctional implantable structure, the polymer layer includes polysiloxane-acrylate (PSA).

In one embodiment of the multifunctional implantable structure, the metal layer is biocompatible.

In one embodiment of the multifunctional implantable structure, the metal layer includes at least one selected from a group consisting of gold, silver, titanium, and molybdenum.

In one embodiment of the multifunctional implantable structure, the metal layer is formed by coating an amorphous metal layer on the polymer layer.

In one embodiment of the multifunctional implantable structure, the drug is released through the pores defined in the metal layer.

In one embodiment of the multifunctional implantable structure, the metal layer is controlled in a temperature thereof by near-infrared rays (NIR) to control a release rate of the drug.

According to the present disclosure, the drug may be easily loaded in the pores of the polymer layer due to the large surface area of the nano-turf structure.

Since the pore size, depth, etc. in the nano-turf structure may be easily controlled, the amount of the drug that may be loaded therein may be controlled, and personalized release of the loaded drug may also be achieved.

The metal layer works as the passivation layer such that the drug may be easily loaded in the polymer layer.

When the near infrared rays are applied to the metal layer, the temperature of the metal layer is increased. Thus, by controlling this temperature increase of the metal layer, the release of the drug may be controlled quantitatively.

The selective cell proliferation inhibition may lead to inhibition of proliferation of tumor cells via control of the cell adhesion to the nano-turf structure of the polymer layer.

Using the dip coating method to form the polymer layer on the implantable base may allow the polymer layer to be easily coated on the flexible and curved base.

The present disclosure may be applied to various application fields such as an implantable device, a drug delivery device, and a functional biomaterial selectively inhibiting cell proliferation.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTIONS OF THE DRAWINGS

Figure 1:
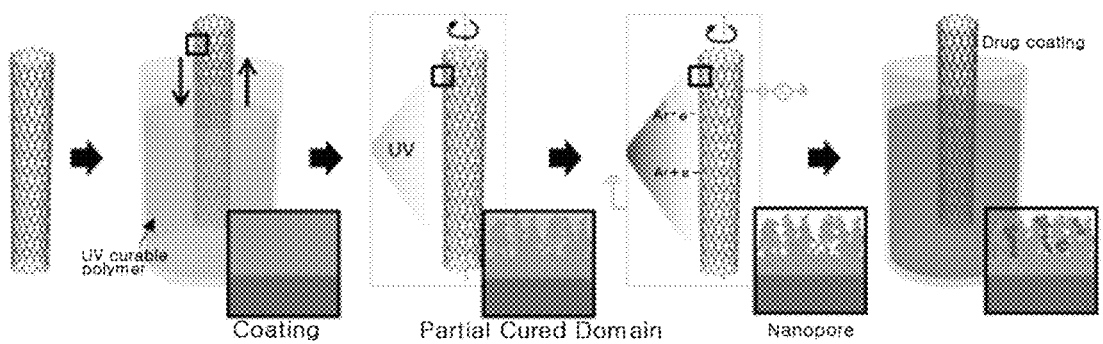
FIG. 1 shows a schematic diagram of a method for producing an implantable structure according to an embodiment of the present disclosure.

For simplicity and clarity of illustration, elements in the figures are not necessarily drawn to scale. The same reference numbers in different figures denote the same or similar elements, and as such work similar functionality. Also, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented for example, rotated 90 degrees or at other orientations, and the spatially relative descriptors used herein should be interpreted accordingly.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A method for producing a multifunctional implantable structure according to an embodiment of the present disclosure comprises forming a coating layer having different crosslinking degrees using a partially curable polymer, and selectively removing low modulus portions of the coating layer, to provide a functional nanoturf structure having pores defined therein to load a drug or functional substances, wherein the functional nanoturf structure is capable of cell adhesion control thereto for increasing survival of the patient.

A specific producing method of the multifunctional implantable structure comprises: preparing an implantable base; coating a polymer layer on the base, wherein the polymer layer is partially curable; curing the polymer layer such that the polymer layer has cured and non-cured portions; and dry-etching the polymer layer to remove the non-cured portion thereof, to allow the polymer layer to have a nano-turf structure having pores defined therein.

Figure 2:
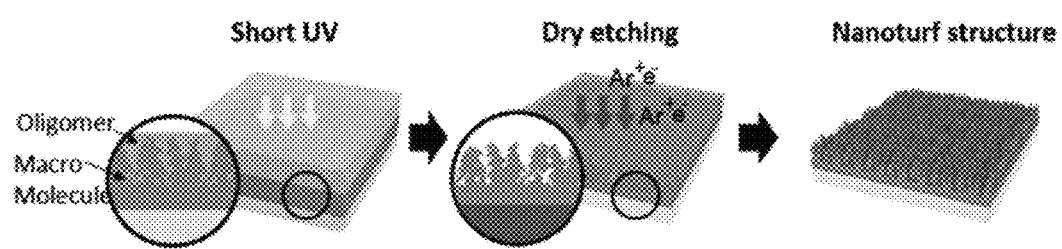
FIG. 2 shows a schematic diagram for schematically explaining characteristics of an implantable structure according to an embodiment of the present disclosure.

Hereinafter, referring to FIG. 1 and FIG. 2, the method of producing the structure in accordance with the present disclosure will be described in detail.

First, the implantable base is prepared.

Then, a polymer layer may be coated on the base. A method of coating the polymer layer is not particularly limited. Any method may be available as long as the method forms the polymer layer in accordance with the present disclosure.

In this connection, the polymer is preferably partially curable. Any polymer may be applied as long as the polymer is partially cured by external stimulus.

In addition, the polymer may be optical curable. It may be cured by external UV.

The polymer may be biodegradable. The biodegradable polymer refers to a polymer material that is converted into a low molecular weight compound by metabolism of an organism during at least one phase of a decomposition process. Ideal biodegradable polymers should exhibit excellent performance during use thereof and be decomposed rapidly by natural microorganisms after disposal. Generally, decomposition of the polymer by microorganisms includes, secreting decomposition enzyme by the microorganism outside the microorganism, adsorbing the enzyme on a surface of the polymer material, hydrolyzing and cleaving chemical bonds such as an ester bond, a glycoside bond, a peptide bond, etc. of the polymer, thereby to allow the polymer to have a low molecular weight. Due to the low molecular weight of the polymer, the polymer material is collapsed and thus changes to a product of a low molecular weight including monomers or dimers via the enzymatic decomposition.

Next, the polymer coating layer is partially cured. At this time, the external stimulus is required for curing. To this end, for example, UV may be used. In this way, some portions of the polymer are cured, and the other portions thereof are left uncured.

Then, the polymer is dry-etched to remove the non-cured portions to porosify the polymer or to form a nanto-turf of the polymer. The non-cured portions are removed by the dry etching from the base, while only the cured coating layer remains on the base. In this connection, the dry etching improves the processing accuracy as compared with a wet etching method, and includes plasma etching, sputter etching, ion etching, and the like. In accordance with the present disclosure, the dry etching is not particularly limited. Any dry etching may be applied as long as the dry etching removes the non-cured polymer potions in accordance with the present disclosure.

In this way, the considerable number of pores are formed, and the drug may be loaded in the pores. The pores are preferably formed at a nano-scale size.

Further, the producing method may further include, after dry etching, immersing the polymer layer in the drug so that the drug is loaded in the pores of the nanoturf structure. The above drug may include various drugs based on applications of the present disclosure. The polymer layer may be immersed in a solution containing the drug. Alternatively, the drug may be directly loaded in the polymer. In this manner, the drug may be injected into the pores so that the nano-turf structure may carry the drug.

The method may further comprises, after the immersing, coating a metal layer as a passivation layer on the polymer layer.

In this connection, the passivation means protecting the surface of the polymer layer in which the drug is loaded.

The metal layer is preferably biocompatible. The term "biocompatible metal" refers to a substance that does not adversely affect the living body when it is implanted into the living body or adhered to the living body and may be compatible with the living body while working its original functions. The metal layer includes at least one selected from the group consisting of gold, silver, titanium, and molybdenum.

The metal layer is preferably formed by coating the amorphous metal layer on the polymer layer. In one example, the metal layer is formed by sputtering. It is preferable that the metal layer also has pores defined therein. Moreover, the drug is released through the pores defined in the metal layer.

In particular, the metal layer is a thin metal layer which does not affect a cell intimacy of the structure. Nano-sized pores may be defined in the metal layer using vacuum sputtering, so that the drug may be loaded in the pores may be delivered in a controlled manner. Further, the delivery of the drug depends on a diffusion coefficient of the drug, and the diffusion coefficient of the drug is related to the ambient temperature. When the temperature of the metal layer is changed by an external heat source, the diffusion coefficient of the drug may be easily changed, and, thus, a drug transfer rate may also be changed. Thus, by controlling the temperature of the metal layer using the near-infrared, the diffusion coefficient of the drug may be controlled, and, thus, the release of the drug may be controlled. NIR (Near-Infrared Red) may be used as the external heat source.

Figure 3:
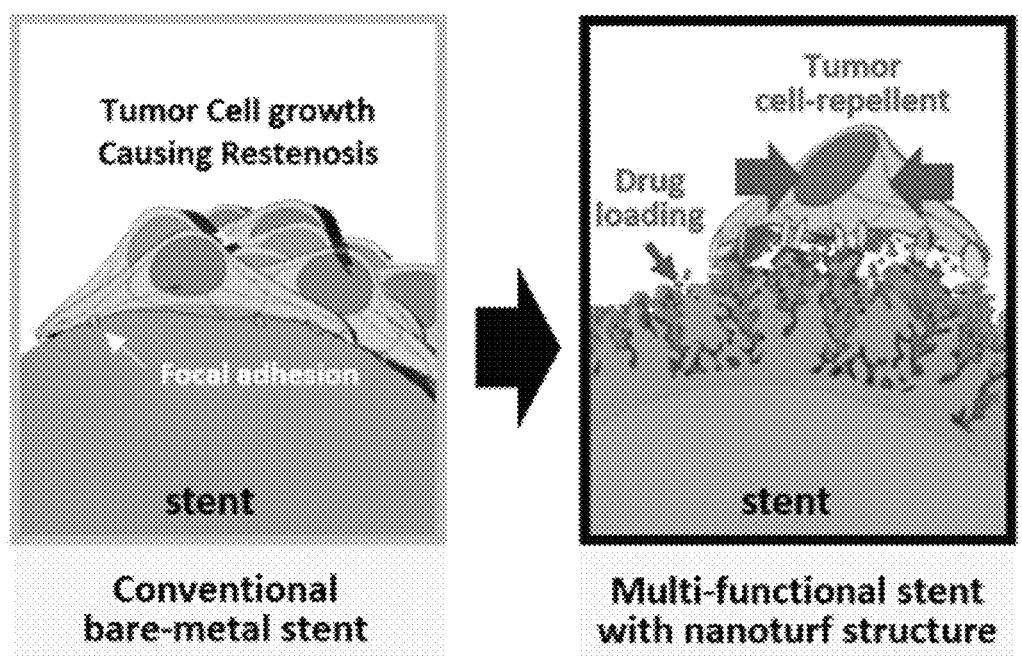
FIG. 3 shows a schematic diagram for schematically explaining characteristics of an implantable structure according to an embodiment of the present disclosure and a conventional implantable structure.

Furthermore, the schematic diagram for schematically explaining the characteristics of a conventional implantable structure and an implantable structure according to an embodiment of the present disclosure is shown in FIG. 3. As shown in FIG. 3, the cancer cells or the tumor cells adhere to a conventional stent to induce restenosis. However, since a stent according to the present disclosure has a metal-cluster, the cancer cells or the tumor cells may not adhere well to the surface of the present stent. Particularly, even when the cancer cells or the tumor cells adhere to the metal-cluster, the cancer cells or the tumor cells may be easily detached because portions of the cancer cells or the tumor cells that are in contact with the pores in the metal-cluster do not adhere to the stent. Further, when the drug loaded in the pores is released, it directly reaches the cancer cells or the tumor cells so that the healing efficacy by the drug may be improved.

In another aspect of the present disclosure, there is provided a multifunctional implantable structure comprising: an implantable base; and a nano-turf structure formed on the base, wherein the nano-turf structure includes: a polymer layer having pore defined therein, and a metal layer formed on the polymer layer, wherein the metal layer has pore defined therein, wherein the pores in the polymer layer are loaded with a drug.

The structure may be produced by one of the methods described above. However, the present disclosure is not limited to such a production method.

Further, the description of the components of the structure as described with reference to the above producing method will be omitted.

The structure having the nano-turf structure has the large surface area per an unit mass. Thus, the structure may load various substances therein. The porous nano-turf structure may efficiently carry the drug produced for targeting the cancer cell, and may control the release rate of the drug. Further, the structure may minimize the damage to a living tissue and effectively treat diseases.

Further, the nano-turf structure may be attached to a bio medical device while is later inserted into the human body. The nano-turf structure may be preferably made of a material having biocompatibility. In this connection, the nano-turf structure may be used as a drug delivery layer for a stent, a biosensor, an artificial heart valve, a ventricular assist device, a therapeutic device, and the like. However, the present disclosure is not limited thereto. The present structure may be applied to any implantable device.

Hereinafter, the present disclosure will be described by way of examples.

EXAMPLE 1

A stent composed of nitinol was immersed in UV partially curable polymer solution to coat the polymer layer on the stent. Thereafter, while rotating the stent, the polymer layer was partially cured by UV. Thereafter, using the dry etching method, the non-cured portion was removed, and the stent with a nano-turf structure having nano-sized pores was obtained.

Figure 4:
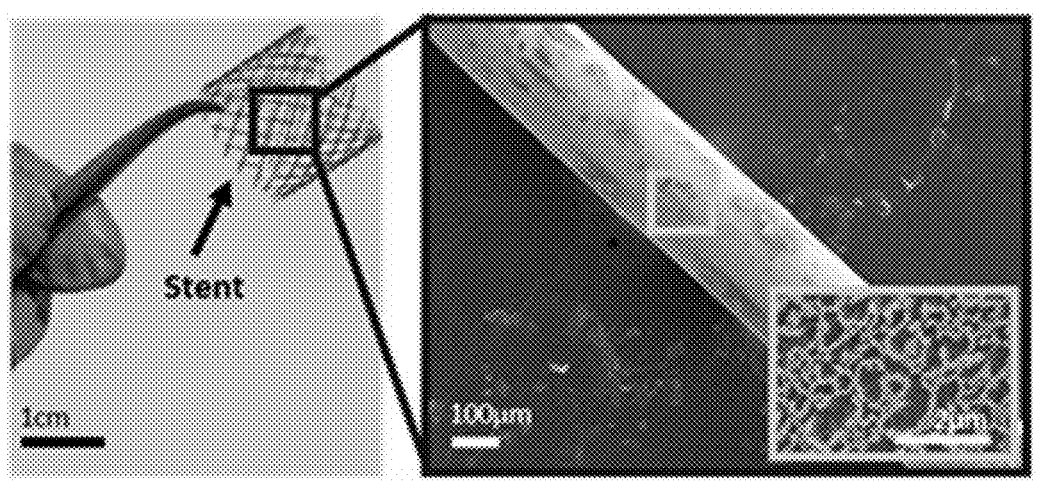
FIG. 4 shows an electron microscope (SEM) image of an implantable structure and a surface thereof according to one embodiment of the present disclosure.

An image and an SEM image of the produced stent are shown in FIG. 4(a) and FIG. 4(b) respectively. As shown in FIG. 4(a) and FIG. 4(b), it was confirmed that uniform pores were formed in the polymer coating layer on the stent.

EXAMPLE 2

Figure 5:
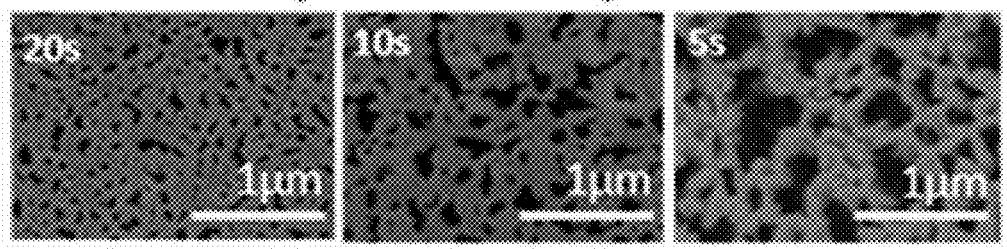
FIG. 5 shows SEM images of implantable structures for a case when a reactive ion etching (RIE) time is constantly controlled during production of the structure and for a case when a UV exposure time is constantly controlled during producing the structure, according to an embodiment of the present disclosure.
Figure 5:

The experiment was conducted again using the same producing method as the producing method as described in the above-mentioned first example. However, in this example, an UV exposure time is different from an reactive ion etching (RIE) time. When the RIE time is constantly controlled, the SEM image of the formed stent is shown in FIG. 5(a). When the UV exposure time is constantly controlled, the SEM image of the formed stent is shown in FIG. 5(b).

As shown in FIG. 5(a) and FIG. 5(b), it was confirmed that the thickness and depth of the nanostructure or pores may be easily controlled.

EXAMPLE 3

Figure 6:
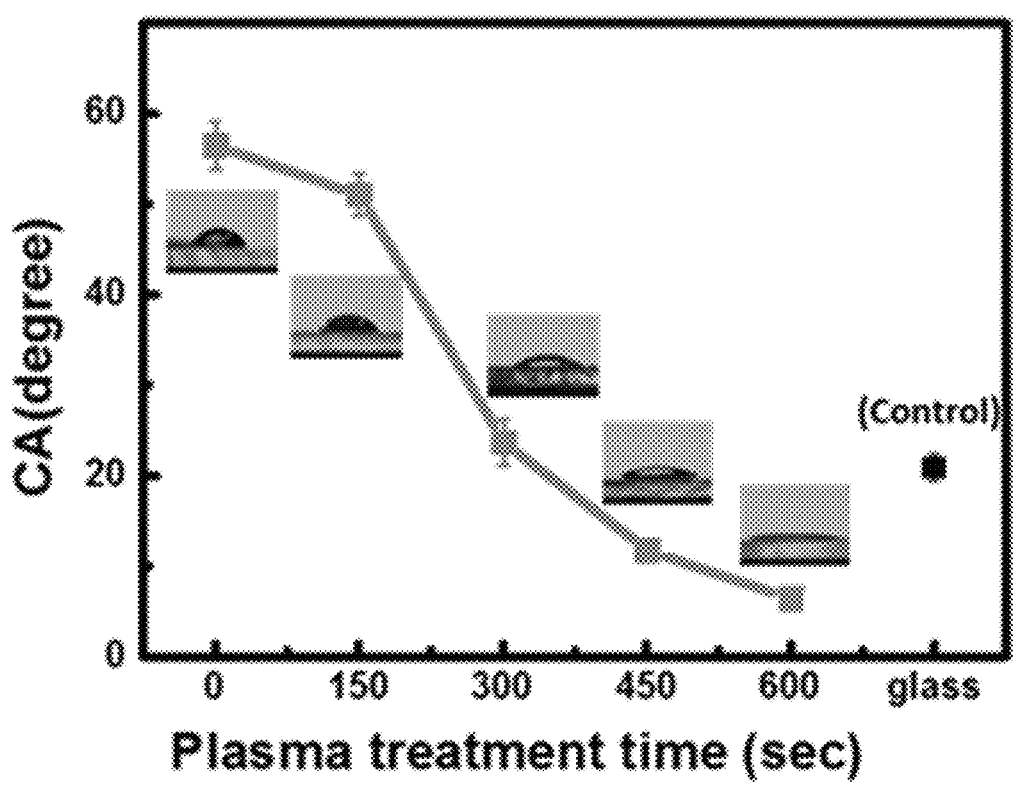
FIG. 6 shows a graph showing a variation of a contact angle (CA) for the nano-turf polymer layers with different plasma treatments, according to an embodiment of the present disclosure, and a contact angle for a glass (control).

In order to confirm the wettability of the structure, additional experiments were conducted while controlling the plasma time. The result graph is shown in FIG. 6. As shown in FIG. 6, it was confirmed that as the depth of the polymer layer becomes deeper, the surface of the structure is more hydrophilic.

It is also known that the greater the wettability of the structure on the cells, the better the adhesion of the structure to the cell. As shown in FIG. 6, the contact angle (CA) of the glass was similar to the CA of a surface of the structure as has been RIE-treated at 21° C. for about 300 seconds. However, in spite of the similar CAs, the cell adhesion differs between the glass and the present structure. From this, it is possibly confirmed that the cell adhesion control factor is not only the wettability but also the cell adhesion is controlled by the polymer layer itself.

EXAMPLE 4

For loading the drug, the stent produced in the Example 1 was immersed in the drug containing solution, to load the drug into the pores formed in the polymer layer. In this connection, the drug was Doxorubicin. The SEM images of the stent with nano-sized pores, the drug-loaded stent, and the drug-releasing stent are shown in FIG. 7.

Figure 7:
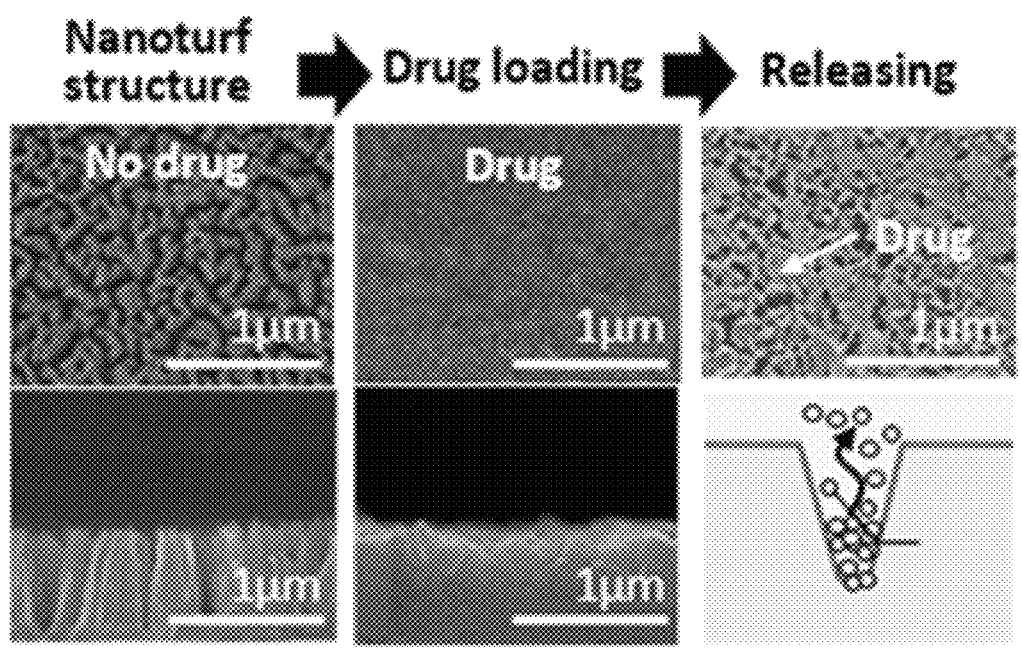
FIG. 7 shows a SEM image showing that a drug in a form of nanoparticles dispersed in water is uniformly loaded (coated) and released due to the variation of the contact angle as shown in FIG. 6.

As shown in FIG. 7, the drug in a form of nanoparticles dispersed in water was loaded and diffused without a further surface treatment.

EXAMPLE 5

In addition, in order to control conditions for controlling drug release without causing deformation of the structure, a gold layer was formed on the drug loaded structure in Example 4 above. The gold coating layer acts as a passivation layer. The schematic diagram thereof was shown in FIG. 8. A graph illustrating a cumulative release amount of the drug versus time based on a coating layer thickness is additionally shown in FIG. 8.

Figure 8:
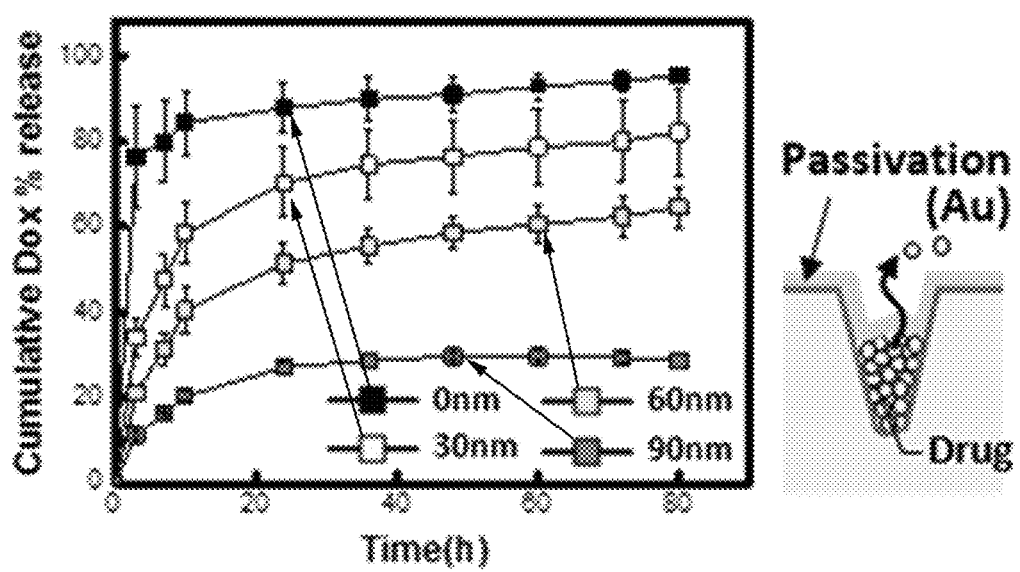
FIG. 8 shows a graph showing a degree of drug release delay with respect to a thickness of a metal layer of an implantable structure according to an embodiment of the present disclosure.

As shown in FIG. 8, It was confirmed that the thin metal layer has delayed the drug release.

EXAMPLE 6

Figure 9:
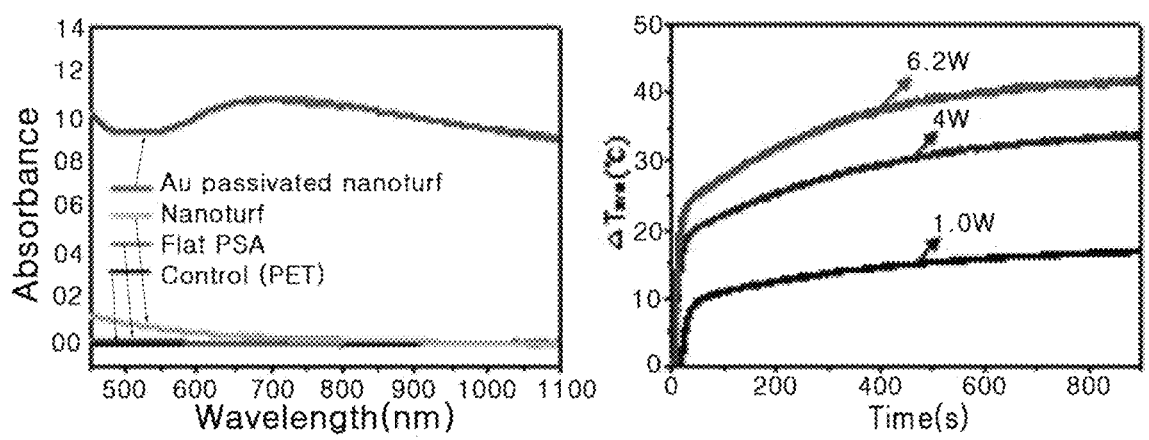
FIG. 9 shows a graph showing an absorbance versus a wavelength and a graph showing a temperature versus a time based on a light intensity, when a heating system irradiates a near-infrared laser onto a metal layer of an implantable structure according to an embodiment of the present disclosure.

The stent produced in Example 5 was used to execute further experiments where a heating system is applied to heat the metal layer. FIG. 9 shows the temperature of the metal layer versus time while varying the applied near-infrared intensity.

As shown in FIG. 9, it was confirmed that the temperature of the stent increases as the near-infrared intensity increases. From this, it was confirmed that a drug release rate at a target amount from the structure is adjusted by the joule-heating system.

EXAMPLE 7

Figure 13:
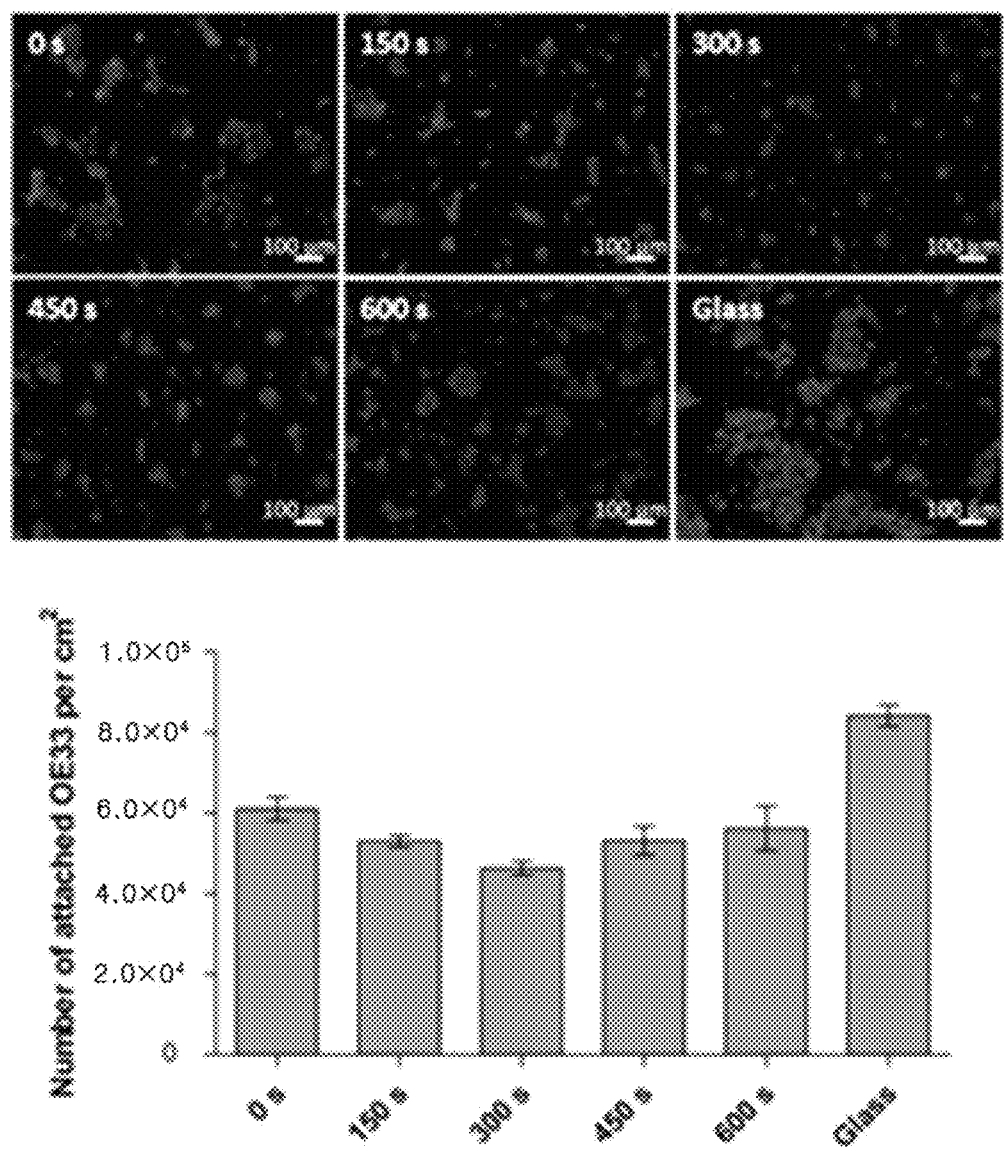
FIG. 13 shows fluorescent images of esophageal cancer cells with stained nucleus as grown on implantable structures produced under various conditions, and a graph illustrating the number of the esophageal cancer cells, according to the present disclosure.

In order to demonstrate that the present structure has cell adhesion control as well as drug loading and releasing control, the stent was produced in the same manner as in Example 5 except conditions as described below. OE33 (human oesophageal adenocarcinoma cell line) was grown on the stent. A scanning electron microscope (SEM) image, and a fluorescent image of esophageal cancer cells deposited on the stent, and the number of adherent cells as measured over a time are shown in FIG. 10, FIG. 11 and FIG. 13 respectively.

Figure 10:
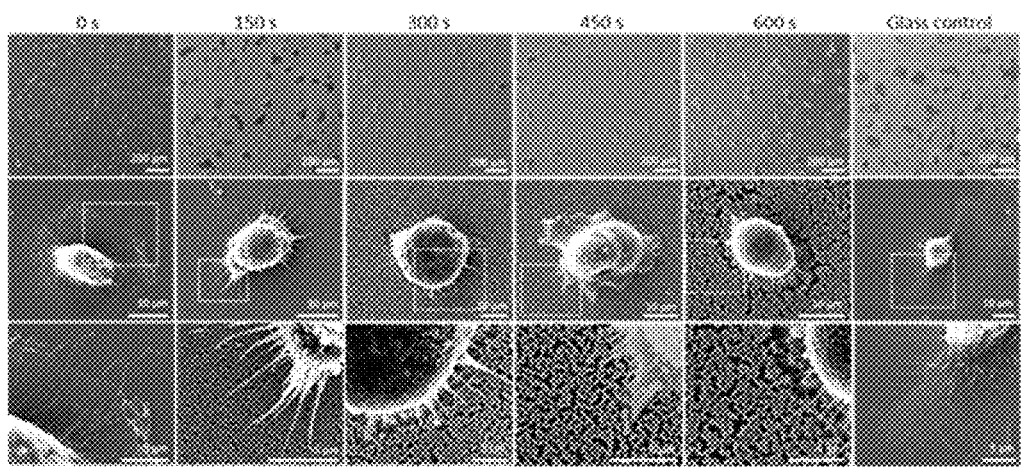
FIG. 10 shows a scanning electron microscope (SEM) image of esophageal cancer cells grown on implantable structures produced under various conditions, according to the present disclosure.
Figure 11:
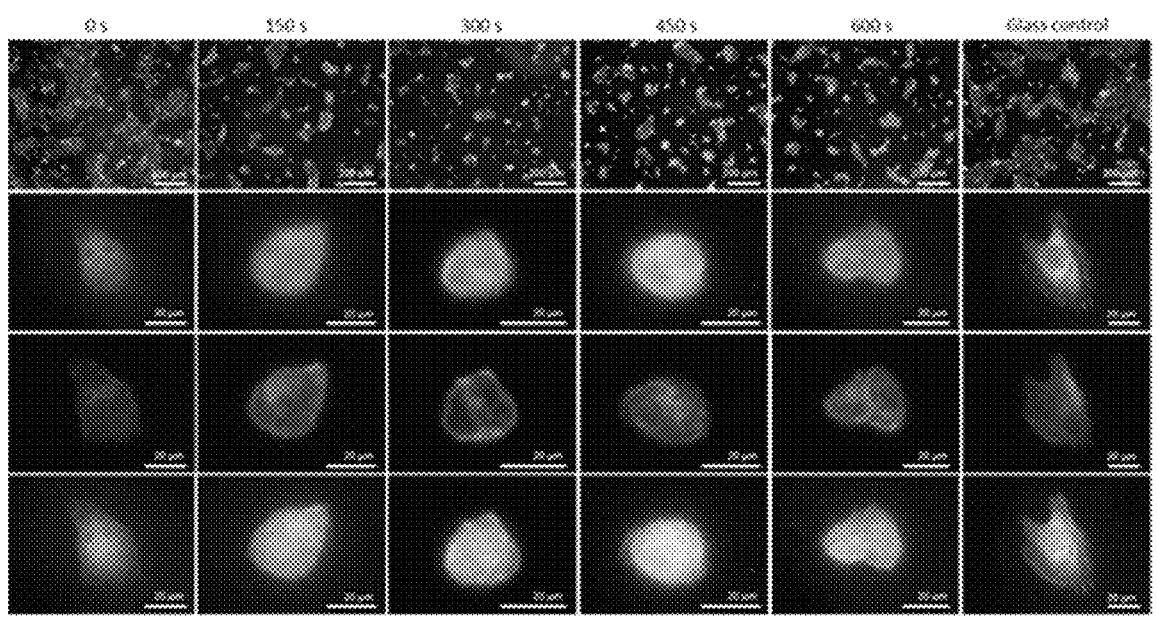
FIG. 11 shows fluorescent images of esophageal cancer cells grown on implantable structures produced under various conditions, according to the present disclosure.

As shown in FIG. 10, for the structure in accordance with the present disclosure, focal adhesion was lower than that of a flat glass. Furthermore, as shown in FIG. 11, it was confirmed that, for the structure in accordance with the present disclosure, the esophageal cancer cells were more circular compared to the glass. In addition, as shown in FIG. 13, it was confirmed that, for the structure in accordance with the present disclosure, an adhesion area of the esophageal cancer cells decreased by up to 50% as compared with the flat glass.

EXAMPLE 8

Figure 12:
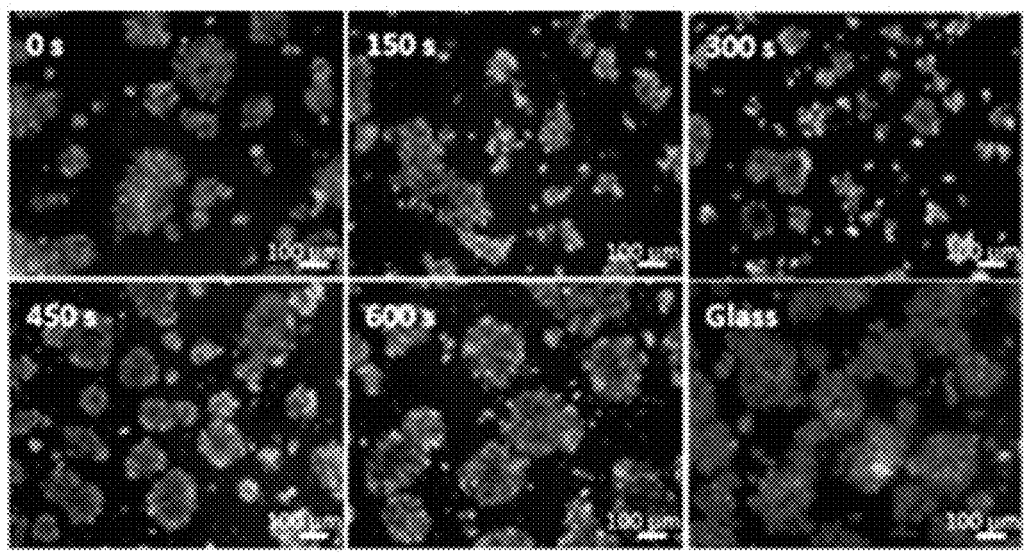
FIG. 12 shows results of live/dead cell viability assay of esophageal cancer cells grown on implantable structures produced under various conditions, according to the present disclosure.
Figure 12:
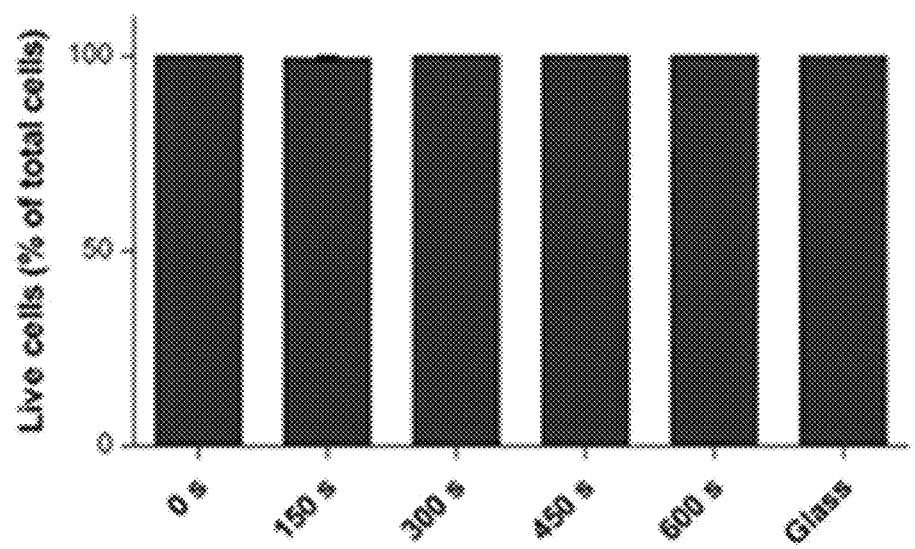

In order to confirm the biocompatibility of the structure, a live/dead cell viability assay test was conducted on the stent produced in Example 7. In FIG. 12, the live/dead cell viability assay results for the cells grown on the structure are shown. In this connection, an adsorption degree of proteins on the structure are shown using a fluorescent image and a graph indicating a fluorescent intensity.

As shown in FIG. 12, it was confirmed that almost 100% of living esophageal cancer cells as compared with dead cells as deposited on the surface of the structure controlled according to the present disclosure have no toxicity like the dead cells.

EXAMPLE 9

Figure 14:
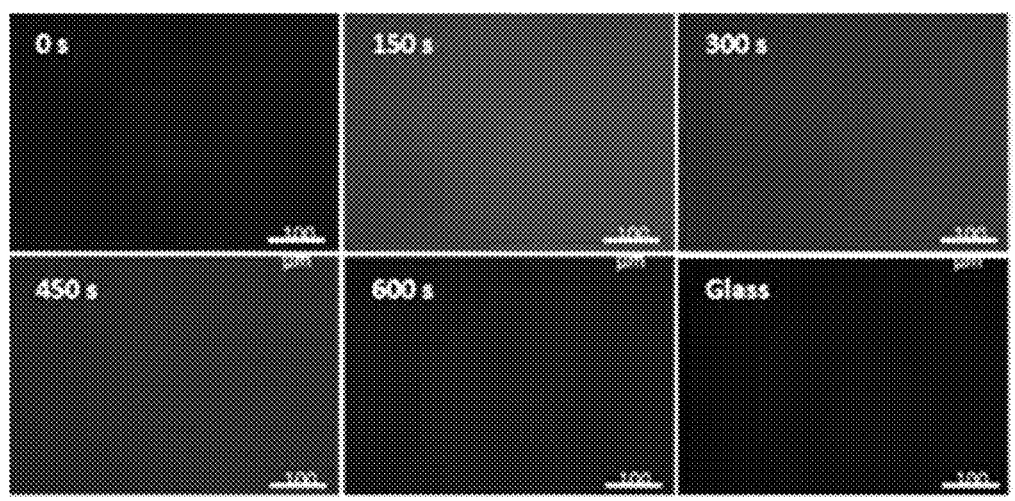
FIG. 14 shows a fluorescent image illustrating adsorption degrees of proteins onto implantable structures produced under various conditions, and a graph illustrating fluorescent intensities of the proteins, according to the present disclosure.
Figure 14:
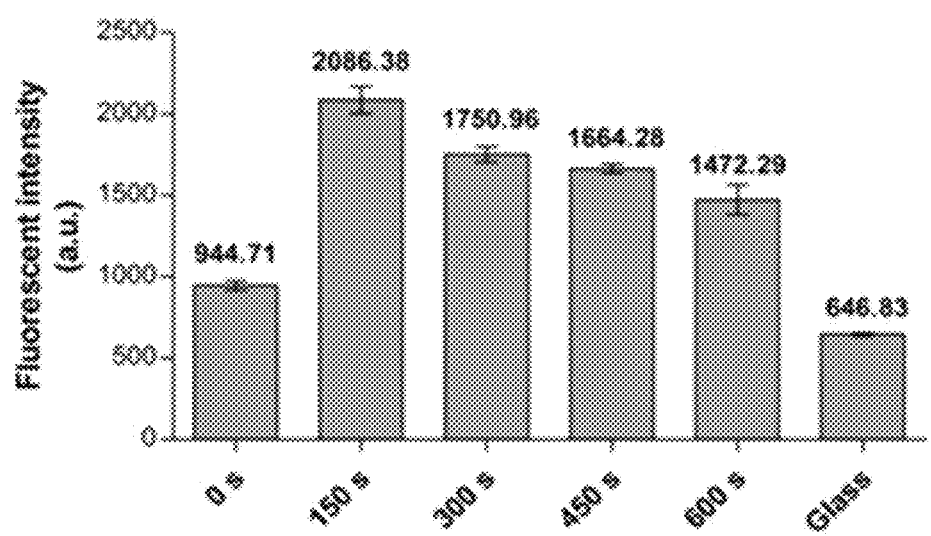

In order to confirm that the adhesion control factor of the esophageal cancer cell mentioned in Example 8 is a structural factor among other factors, proteins capable of cell adhesion thereto were adsorbed on the stent shown in Example 8, and then the amount thereof was measured. FIG. 14 shows a fluorescence image and a fluorescent intensity graph indicating a degree of proteins adsorption on the structure produced under various conditions.

As shown in FIG. 14, it was confirmed that although the smallest amount of proteins was coated on the glass, the largest esophageal cancer cells adhere to the glass. From this, it was found that the cell adhesion was affected not by the protein capable of cell adhesion thereto but by the structure of the glass.

Although the above description has been made with reference to the preferred embodiments of the present disclosure, those skilled in the art will readily recognize that various modifications and changes may be made thereto without departing from the spirit and scope of the present disclosure as set forth in the following claims.

What is claimed is:

1. A method for producing a multifunctional implantable structure, the method comprising:
   preparing an implantable base;
   coating a polymer layer on the base, wherein the polymer layer is partially curable;
   curing the polymer layer such that the polymer layer has cured and non-cured portions; and
   dry-etching the polymer layer to remove the non-cured portions thereof, to allow the polymer layer to have a nano-turf structure having nanopores defined therein,
   further comprising, after the dry-etching, immersing the polymer layer in a drug such that the nanopores are loaded with the drug.

2. The method according to claim 1, further comprising, after the immersing, coating a metal layer as a passivation layer on the polymer layer.

3. The method according to claim 1, wherein the polymer layer is photo-curable.

4. The method according to claim 1, wherein the polymer layer is biodegradable.

5. The method according to claim 2, wherein the metal layer is biocompatible.

6. The method according to claim 2, wherein the metal layer comprises at least one selected from a group consisting of gold, silver, titanium, and molybdenum.

7. The method according to claim 2, wherein coating the metal layer includes coating an amorphous metal layer on the polymer layer.

8. The method according to claim 2, wherein the metal layer has pores defined therein, wherein the drug is released through the pores defined in the metal layer.

9. The method according to claim 2, wherein the temperature of the metal layer is controlled by near-infrared rays (NIR) to control a release rate of the drug.

10. The method according to claim 1, wherein at least a part of the non-cured portions extends only partially in the thickness direction of the polymer layer.

11. The method according to claim 1, wherein the curing is optical curing.

12. A method for producing a multifunctional implantable structure, the method comprising:
  preparing an implantable base;
  coating a polymer layer on the base, wherein the polymer layer is partially curable;
  curing the polymer layer such that the polymer layer has cured and non-cured portions; and
  dry-etching the polymer layer to remove the non-cured portions thereof, to allow the polymer layer to have a nano-turf structure having nanopores defined therein,
  further comprising, alter the dry-etching, immersing the polymer layer in a drug such that the nanopores are loaded with the drug, wherein the polymer layer includes polysiloxane-acrylate (PSA).

13. A method for producing a multifunctional implantable structure, the method comprising:
  coating a polymer layer on an implantable nitinol base, wherein the polymer layer comprises polysiloxane-acrylate and is partially curable;
  curing the polymer layer with UV curing such that the polymer layer has cured and non-cured portions;
  dry-etching the polymer layer to remove the non-cured portions thereof, to obtain on the polymer layer a nano-turf structure having nanopores defined therein; and
  loading a drug into the nanopores to obtain a drug-loaded porous structure.

14. A method of producing an implantable structure, comprising:
  coating a polysiloxane-acrylate (PSA) polymer material on at least a surface of a biocompatible substrate to obtain a coated PSA polymer layer;
  partially curing the coated PSA polymer layer to control cross-linking in the coated PSA polymer layer such that the degree of cross-linking in the coated PSA polymer layer varies in at least a thickness direction of the coated PSA polymer layer to obtain a partially-cured PSA polymer layer having a surface that comprises removable portions and non-removable portions, wherein at least some of the removable portions extend less than fully through the partially-cured PSA polymer layer in the thickness direction of the partially-cured PSA polymer layer;
  dry-etching the partially-cured PSA polymer layer to remove the at least some of the removable portions to obtain pores defined by the non-removable portions remaining on the surface of the partially-cured PSA polymer layer; and
  loading a drug into the pores to obtain a drug-loaded porous structure.

15. The method according to claim 14, wherein the dry-etching the partially-cured PSA polymer layer further comprises controlling the time duration of the dry-etching to control a width dimension of the pores.

16. The method according to claim 14, wherein the partially curing the coated PSA polymer layer further comprises controlling the time duration of the partially curing to control a depth dimension of the pores.

17. The method according to claim 14, wherein the pores have a nano-scale size.

18. The method according to claim 14, further comprising coating a passivation layer on the drug-loaded porous structure, wherein the passivation layer comprises a biocompatible metal surface having nano-sized pores formed therein.

19. The method according to claim 18, wherein the coating the passivation layer further comprises controlling a thickness of the passivation layer to control a drug-release property of the implantable structure.

* * * * *